US011893871B2

(12) United States Patent
McEwen et al.

(10) Patent No.: US 11,893,871 B2
(45) Date of Patent: Feb. 6, 2024

(54) GAS DETECTOR WITH VISUAL COMPLIANCE VERIFICATION

(75) Inventors: Shane Lee McEwen, Calgary (CA); Phillip W. Benson, Calgary (CA); Clive W. Kennard, Alberta (CA); Arun Bhargava, Alberta (CA)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 820 days.

(21) Appl. No.: 12/550,976

(22) Filed: Aug. 31, 2009

(65) Prior Publication Data
US 2011/0048100 A1 Mar. 3, 2011

(51) Int. Cl.
*G01N 33/00* (2006.01)
*G08B 21/14* (2006.01)
*G08B 29/20* (2006.01)

(52) U.S. Cl.
CPC ......... *G08B 21/14* (2013.01); *G01N 33/0006* (2013.01); *G08B 29/20* (2013.01)

(58) Field of Classification Search
CPC .......... G01N 33/0006; G01N 27/4163; G08B 21/16; G08B 21/14; G08B 21/12; G08B 17/10; G08B 21/182; G08B 29/26
USPC ..... 73/23.2, 23.3, 23.31, 23.32, 23.34, 31.1, 73/31.02, 31.03, 31.05, 431, 866.3
See application file for complete search history.

(56) References Cited

U.S. PATENT DOCUMENTS

| | | | |
|---|---|---|---|
| 4,428,685 A * | 1/1984 | Lemelson | G01B 3/18 374/163 |
| 6,182,497 B1 * | 2/2001 | Krajci | G01N 33/0075 340/605 |
| 6,244,093 B1 * | 6/2001 | Parekh | G01N 33/0006 73/1.06 |
| 6,411,207 B2 * | 6/2002 | Shaffer | G08B 7/06 340/521 |
| 6,428,684 B1 * | 8/2002 | Warburton | G01N 27/4163 204/401 |
| 6,442,639 B1 * | 8/2002 | McElhattan | G01N 33/0006 710/303 |
| 6,744,373 B2 * | 6/2004 | Koyano | G08B 21/14 324/464 |
| 7,159,445 B2 * | 1/2007 | Bohm | G01M 3/205 73/23.2 |

(Continued)

FOREIGN PATENT DOCUMENTS

BR PI1003023 A2 9/2015
CA 2712899 A1 2/2011
(Continued)

OTHER PUBLICATIONS

ToxiRAE 3 User's Guide Revision C, Rae Systems, May 2008. (Year: 2008).*

(Continued)

*Primary Examiner* — Peter J Macchiarolo
(74) *Attorney, Agent, or Firm* — Alston & Bird LLP

(57) ABSTRACT

A multi-sensor gas detector includes circuitry to evaluate if the detector is in compliance with predetermined safety requirements. Where the detector is in compliance, then a confidence indicator is intermittently activated at a predetermined frequency. Where the detector is out of compliance, the indicator is not activated providing indicia that the detector needs maintenance.

12 Claims, 3 Drawing Sheets

(56) References Cited

U.S. PATENT DOCUMENTS

| | | | | |
|---|---|---|---|---|
| 7,275,411 | B2* | 10/2007 | Peng | G01N 1/2226 73/1.03 |
| 7,279,688 | B2* | 10/2007 | Campman | G01N 21/645 250/301 |
| 7,281,404 | B2* | 10/2007 | Peng | G01N 33/00 73/1.06 |
| 7,319,385 | B2* | 1/2008 | Ruha | A61B 5/02055 340/539.12 |
| 7,378,954 | B2* | 5/2008 | Wendt | G01D 9/005 340/539.11 |
| 7,530,255 | B2* | 5/2009 | Frank | G01N 33/0006 73/1.03 |
| 7,623,028 | B2* | 11/2009 | Kates | G01N 33/0065 340/521 |
| 7,661,290 | B2* | 2/2010 | Gu | G01N 33/0006 73/1.03 |
| 8,537,020 | B2* | 9/2013 | Thorson | G08B 17/10 340/632 |
| 2001/0018844 | A1* | 9/2001 | Parekh | G01N 33/0006 73/1.06 |
| 2001/0050612 | A1* | 12/2001 | Shaffer | G08B 7/06 340/521 |
| 2003/0145644 | A1 | 8/2003 | Rabbett et al. | |
| 2004/0007195 | A1* | 1/2004 | Grewal | F01L 1/344 123/90.17 |
| 2004/0055359 | A1* | 3/2004 | Ketler | G01N 33/0006 73/1.07 |
| 2006/0081033 | A1* | 4/2006 | Peng | G01N 1/2226 73/31.05 |
| 2006/0101925 | A1* | 5/2006 | Peng | G01N 33/00 73/864.41 |
| 2007/0241261 | A1* | 10/2007 | Wendt | G01D 9/005 250/221 |
| 2007/0296569 | A1 | 12/2007 | Bray et al. | |
| 2008/0156074 | A1* | 7/2008 | Tobias | G01N 33/0006 73/25.03 |
| 2009/0113984 | A1 | 5/2009 | Gautieri et al. | |

FOREIGN PATENT DOCUMENTS

| | | |
|---|---|---|
| CN | 100426334 C | 10/2008 |
| CN | 102004140 A | 4/2011 |
| EP | 2293267 A1 | 3/2011 |
| EP | 2293267 B1 | 7/2013 |
| JP | 2007132701 | 5/2007 |
| KR | 20110023765 A | 3/2011 |
| KR | 20170133298 A | 12/2017 |
| WO | 0182063 A1 | 11/2001 |
| WO | WO 01/82063 A1 | 11/2001 |

OTHER PUBLICATIONS

X5 Personal Gas Detector Operating Manual Revision 1, Feb. 2008. (Year: 2008).*
GasAlert100 H2S or CO 100 Day Disposable Gas Detector, BW Technologies, available online at least as early as May 15, 2008. (Year: 2008).*
GasAlert100 100 Day Disposable Gas Detector Instruction Sheet, BW Technologies, Copyright Sep. 2002, available online at least as early as May 15, 2008. (Year: 2008).*
GasAlertClip Extreme 2 or 3 Year Gas Detector Instruction Sheet, BW Technologies, Copyright 2005, available online at least as early as May 15, 2008. (Year: 2008).*
GasAlertClip Extreme H2S, Co, SO2, or O2 2 Year Gas Disposable Gas Detector, BW Technologies, available online at least as early as May 15, 2008. (Year: 2008).*
GasAlert LEL Combustible Gas and Vapors Combustible Gas Detector 0-100% LEL, BW Technologies, available online at least as early as May 15, 2008. (Year: 2008).*
GasAlertMax Gas Detector User Manual, BW Technologies, Copyright 2001, dated Dec. 2002, available online at least as early as May 15, 2008. (Year: 2008).*
GasAlertMicro H2S, CO, O2, SO2, Combustibles 1, 2, 3, and 4 Gas Detectors User Manual, BW Technologies, Copyright 2002, available online at least as early as May 15, 2008. (Year: 2008).*
GasAlertMicro multi-gas detector Datasheet, BW Technologies by Honeywell, available online at least as early as May 15, 2008. (Year: 2008).*
GasAlertMicro 5 H2S, CO, O2, SO2, PH3, NH3, NO2, HCN, CI2, CIO2, O3, Combustibles 5 Gas Detector, BW Technologies, available online at least as early as May 15, 2008. (Year: 2008).*
GasAlertMicro 5 O2, CO, H2S, PH3, SO2, CI2, NH3, NO2, HCN, CIO2, O3, VOC, and Combustibles 1, 2, 3, 4, and 5 Gas Detectors User Manual, BW Technologies, Copyright 2005, available online at least as early as May 15, 2008. (Year: 2008).*
GasAlertMicro 5 VOCs (PID), H2S, CO, O2, SO2, PH3, NH3, NO2, HCN, CI2, CIO2, O3, and Combustibles 5-Gas Detector, BW Technologies, available online at least as early as May 15, 2008. (Year: 2008).*
GasAlertMicroClip H2S, CO, O2, Combustibles Multi-Gas Detector, BW Technologies by Honeywell, available online at least as early as May 15, 2008. (Year: 2008).*
GasAlertMicroClip multi-gas detector Datasheet, BW Technologies by Honeywell, Copyright 2008, available online at least as early as May 15, 2008. (Year: 2008).*
GasAlertMicro H2S, CO, O2, SO2, Combustibles Multi-Gas Detector Datasheet, JJS Technical Services, available online at least as early as May 15, 2008. (Year: 2008).*
GasAlertMicro H2S, CO, O2, SO2, Combustibles 1, 2, 3, and 4 Gas Detectors Quick Reference Guide, BW Technologies, Copyright 2005, available online at least as early as May 15, 2008. (Year: 2008).*
GasAlert Extreme H2S, CO, O2, SO2, PH3, CI2, NH3, NO2, HCN, ETO, CIO2, O3, NO Single-Gas Detectors, BW Technologies, available online at least as early as May 15, 2008. (Year: 2008).*
GasAlert Extreme O2, CO, H2S, PH3, SO2, CI2, NH3, HCN, ETO, CIO2, O3, or NO Single-Gas Detector Quick Reference Guide, BW Technologies by Honeywell, Copyright 2005, available online at least as early as May 15, 2008. (Year: 2008).*
GasAlertMicro 5 and GasAlertMicro 5 PID O2, CO, H2S, PH3, SO2, CI2, NH3, HCN, CIO2, O3, VOC, and Combustibles 1, 2, 3, 4, and 5 Gas Detectors User Manual, BW Technologies, Copyright 2006, available online at least as early as May 15, 2008. (Year: 2008).*
GasAlertMicroClip H2S, CO, O2, Combustibles 1, 2, 3, and 4 Gas Detectors User Manual, BW Technologies by Honeywell, Copyright 2007, available online at least as early as May 15, 2008. (Year: 2008).*
GasAlertMicro H2S, CO, O2, Combustibles 1, 2, 3, and 4 Gas Detectors User Manual, BW Technologies, Copyright 2005, available online at least as early as May 15, 2008. (Year: 2008).*
Partial File Directory from JJS Technical Services, Inc. Listing Document Uploads at least as early as May 15, 2008. (Year: 2008).*
Listing of Gas Detectors/Analyzers Available From Instrumart Industrial Instrument Superstore, available online at the Internet Archive <https://web.archive.org/web/20080511150950/http://www.instrumart.com/ProductList.aspx?CategoryID=4892& ManufacturerID=1123>, May 11, 2008. (Year: 2008).*
Honeywell Analytics Distribution, Inc.: Gas Detection Instrumentation, BNP Media and available online at <https://www.achrnews.com/articles/106719-honeywell-analytics-distribution-inc-gas-detection-instrumentation-2>, Apr. 14, 2008. (Year: 2008).*
Sensing Danger, available online at <https://www.oilandgasmiddleeast.com/article-4938-sensing-danger>, Oct. 26, 2008. (Year: 2008).*
European Search Report corresponding to Application No. EP 10 17 3109, dated Dec. 20, 2010.
Canada Patent Application No. 2,712,899, Office Action, dated Jul. 13, 2017, 5 pages.
Canada Patent Application No. 2,712,899, Office Action, dated Jul. 12, 2016, 3 pages.
Europe Patent Application No. 10173109.9, European Search Report, dated Dec. 28, 2010, 3 pages.
Europe Patent Application No. 10173109.9, Examination Report, dated Jan. 14, 2011, 3 pages.

(56) References Cited

OTHER PUBLICATIONS

Europe Patent Application No. 10173109.9, Intention to Grant, dated Feb. 26, 2013, 5 pages.
China Patent Application No. 2010102678020, Office Action, dated Jan. 24, 2014, 12 pages.
China Patent Application No. 2010102678020, Notification to Grant Patent Right, dated Oct. 9, 2014, 4 pages.
Korean Patent Application No. 20100080369, Notification of Reason for Rejection, dated Jul. 12, 2017, 5 pages.
Canada Patent Application No. 2,712,899, Office Action, dated Aug. 7, 2017, 7 pages.
Korean Patent Application No. 20100080369, Notification of Decision for Rejection, dated Sep. 20, 2017, 2 pages.
Korean Patent Application No. 20100080369, Notice of Decision for Rejection, dated Oct. 30, 2017, 5 pages.
Korean Patent Application No. 20170157806, Office Action, dated Dec. 27, 2017, 22 pages.
Korean Patent Application No. 20170157806, Notice of Decision for Rejection, dated Jul. 30, 2018, 5 pages.
Europe Patent Application No. 10173109.9, Decision to Grant, dated Jun. 13, 2013, 2 pages.

\* cited by examiner

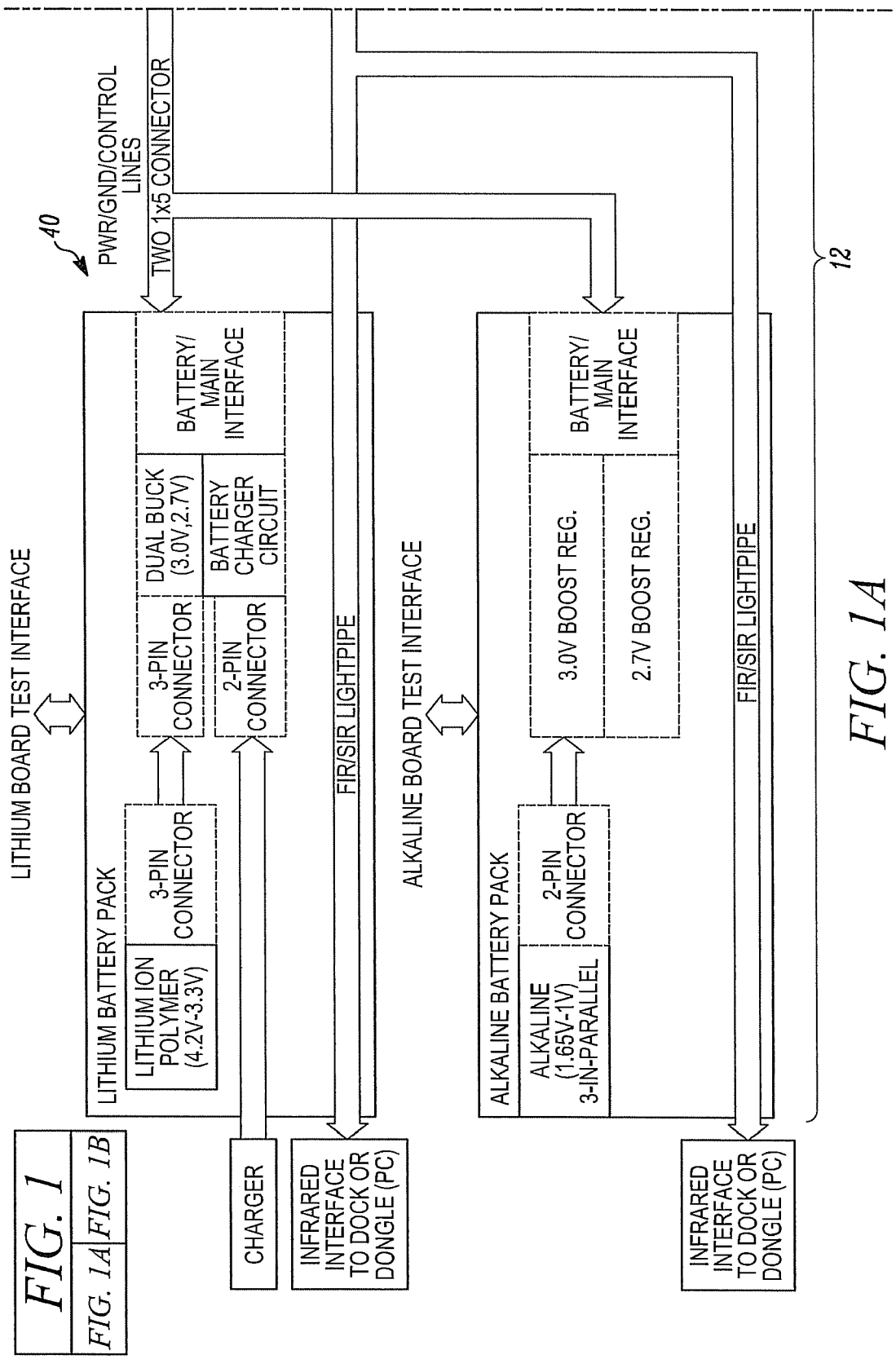

GAS DETECTOR WITH VISUAL COMPLIANCE VERIFICATION

FIELD

The invention pertains to gas detectors. More particularly, the invention pertains to gas detectors which exhibit visual indications that the respective detector is in compliance with organizational safety policies pertaining to testing and calibration.

BACKGROUND

Gas detectors which might be used in toxic or explosive environments are usually periodically checked for compliance with applicable safety standards. Detector audits are often carried out manually to determine if the respective unit(s) is (are) in compliance with the applicable standards.

Such standards include determining if the respective detector has been periodically exposed to a respective gas, or gases, usually known as a bump test. Additionally, periodic calibration is usually required to comply with applicable safety standards. Audits to evaluate compliance, carried out on a detector by detector basis, are both slow and expensive.

There is a need to provide compliance information, substantially automatically, on a detector by detector basis. Preferably such functionality could be provided without altering the form factor, or weight, of such detectors, and without substantially increasing the cost thereof.

DETAILED DESCRIPTION

Figure 1B:
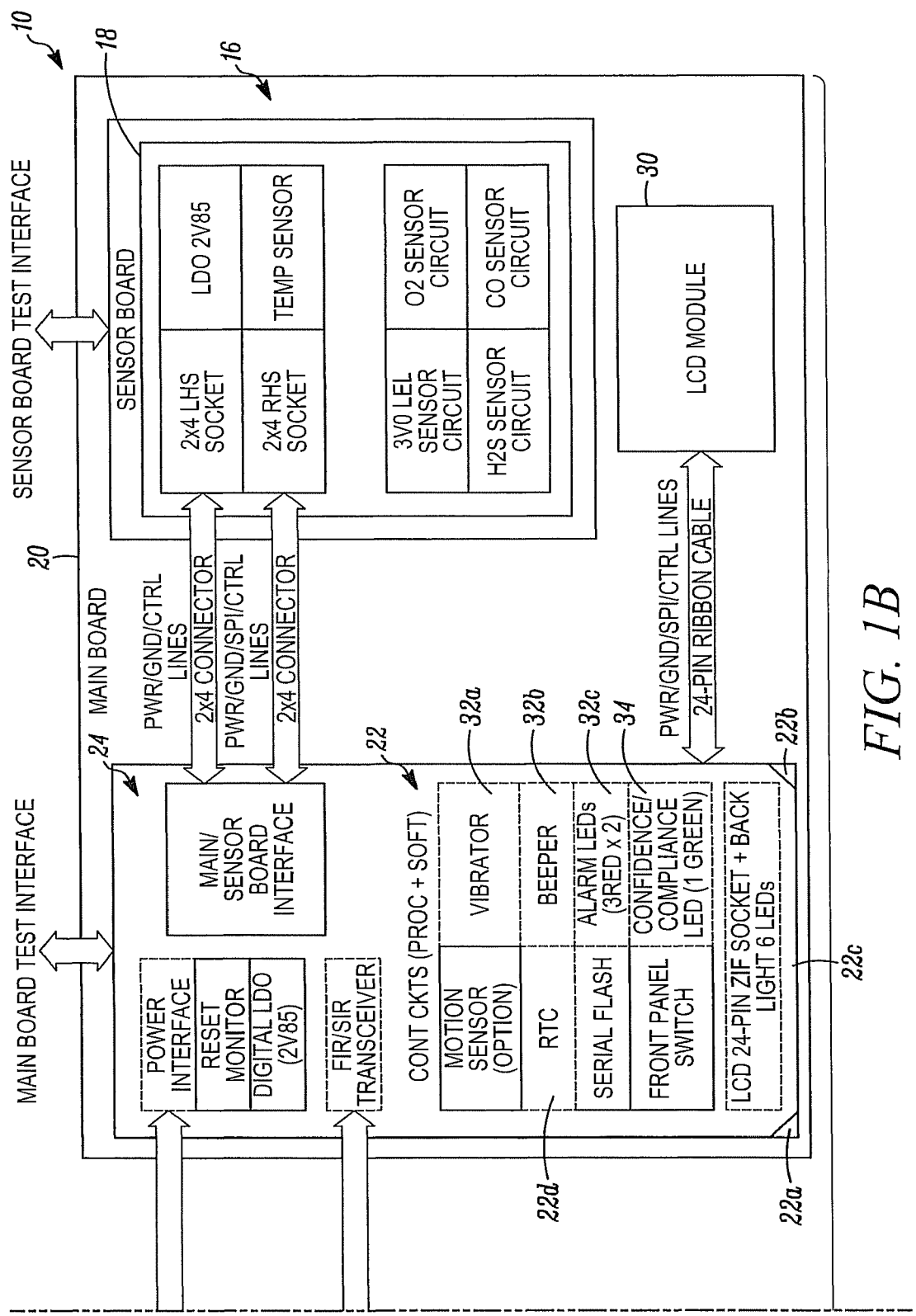
FIG. 1 is a block diagram of a detector which embodies the invention.

While embodiments of this invention can take many different forms, specific embodiments thereof are shown in the drawings and will be described herein in detail with the understanding that the present disclosure is to be considered as an exemplification of the principles of the invention, as well as the best mode of practicing same, and is not intended to limit the invention to the specific embodiment illustrated.

In embodiments of the present detector, information can be stored in the detector as to the last attempt to calibrate the device including whether the calibration attempt was successfully completed. If the last calibration attempt was not successfully completed, a visual and/or audible confidence indicator can be disabled.

Additionally, information can be stored in the detector as to whether the detector successfully completed the last bump test. If the last bump test was not successfully completed, the visual and/or audible confidence indicator can be disabled.

Preferably, only when the last calibration attempt was successfully completed and the last bump test was also successfully completed would the visual and/or audible indicator be activated. For example, in this instance, a green blinking indicator can be provided so long as both conditions are met.

Those of skill in the art will understand that neither the number of gas sensors carried by the detector, nor the respective sensing technologies are limitations of the invention. Additionally, none of the form factor of the detector nor its weight, nor the type of gas level indications provided thereby are limitations of the invention.

In one aspect of the invention, a housing can carry a plurality of gas sensors, and a display device to present gas concentration information visually. Control circuits can be provided coupled to all of the sensors as well as the display device.

Other condition indicating visual devices, such as light emitting diodes (LEDs) can be coupled to the control circuits to provide detector status information apart from gas concentrations and the like. Such status information can include alarm indicators as well as confidence or compliance indicators.

The control circuits can be implemented at least in part, with a programmable processor and associated embedded control software. The processor in combination with the control software, when executed by the processor, can locally store day and time indicia as to when the last calibration was attempted and whether it was successful or not. The day and time of the last attempt to carry out a bump test, as well as test results can also be stored.

So long as the last calibration was successful and another calibration attempt is not over due, and so long as the last bump test was successful and another is not overdue, then the control circuits will intermittently active the confidence or compliance indicator. For example, the respective LED can be periodically blinked to visually indicate that the detector is in compliance. In this regard, a green LED can be periodically energized, blinked, to provide a widely discernable indicium that the detector is in compliance with applicable safety requirements or policies. If not, activation of the green LED is terminated.

Those of skill in the art will understand that operation of the compliance indicating LED or termination thereof will not affect the gas sensing functionality of the detector which will be on-going. However, supervisors and the like in an area will readily be able to visually and easily determine if all detectors in that immediate location are in compliance without having to manually conduct an audit of each. Further, non-compliant detectors can be immediately replaced.

FIG. 1 illustrates an exemplary detector 10 in accordance with the present invention. Detector 10 includes a housing 12 which carries a plurality of different gas, or ambient condition sensors, generally indicated at 16 on a sensor printed circuit board 18.

Sensor board 18 is in communication with main printed circuit board 20 (which carries control circuits 22, including a processor 22a and associated control software 22b), via an interface 24. The control circuits 22 activate a liquid crystal display module 30 to illustrate gas concentrations, or other ambient conditions of interest such as temperature, all without limitation.

Various alarm conditions also can be indicated via vibrator unit 32a, beeper 32b and alarm indicating LEDs, which might emit red light. Compliance, confidence LED, which might emit green light, 34 provides visual indicia (when blinked) that the detector 10 is in compliance, as described above with applicable safety procedures and standards. In the absence of compliance, LED 34 is not activated. Even in the event of non-compliance, control circuits 22 still receive signals from sensors 16, make gas, temperature concentrations and the like and forward appropriate signals to display module 30.

Replaceable batteries 40 energize detector 10. It will be understood that the specific characteristics of batteries 40 are not limitations of the present invention.

Figure 2:
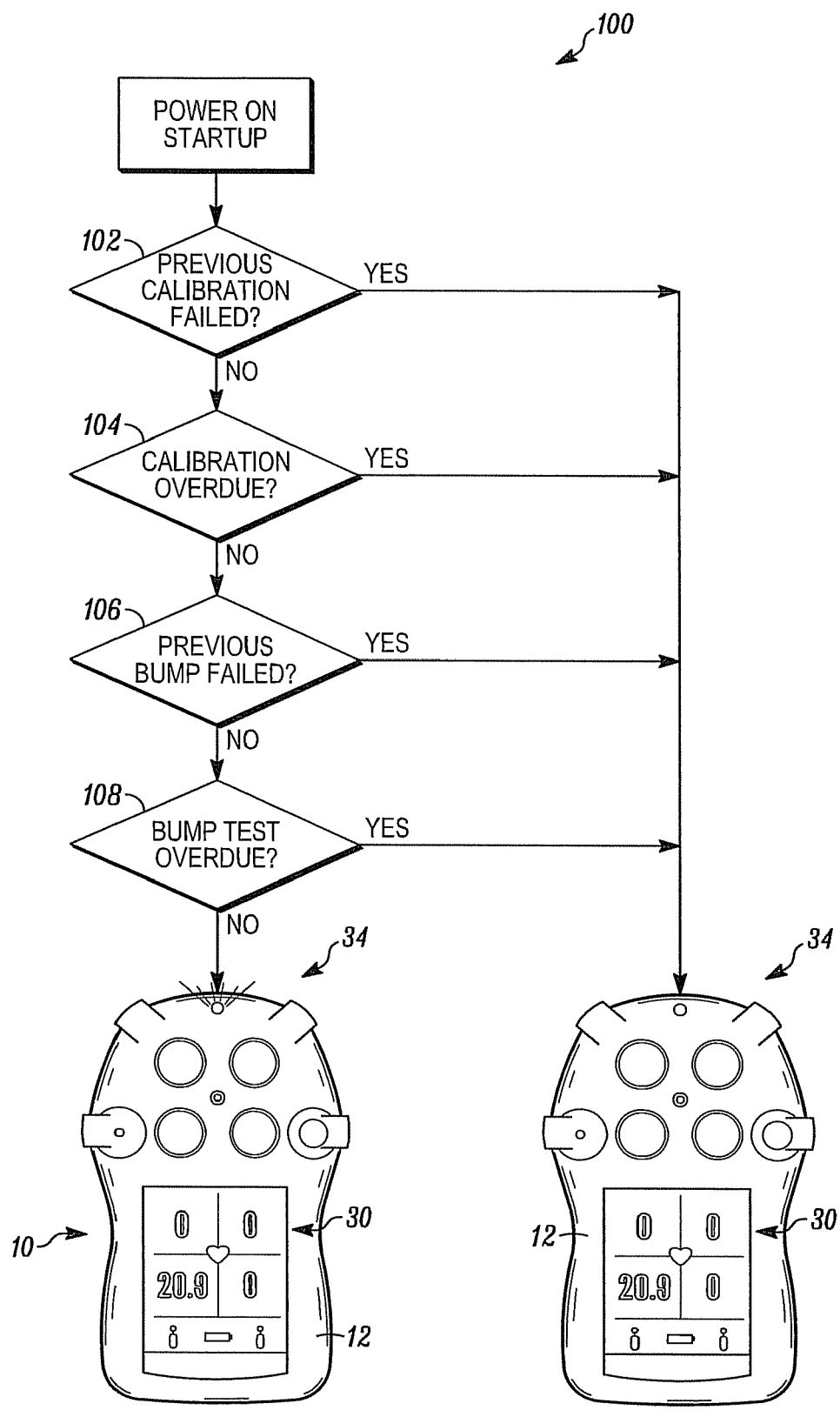
FIG. 2 is a flow diagram which illustrates operational aspects of the detector of FIG. 1.

FIG. 2 illustrates a block diagram of a method 100 of operating the detector 10 in accordance with the invention. During normal detector operation, the control circuits 22 evaluate whether the previous calibration attempt had been successful, as at 102. If so, the control circuits 22 establish if a pre-set time interval, since the last calibration, has passed, as at 104. If it is not time to calibrate the sensors, the control circuits 22 evaluate whether the previous bump test had been a success, as at 106. If the previous bump test was successful, the control circuits establish if a pre-set time interval has passed since the last bump test was carried out, as at 108. If not, the confidence indicator LED 34 is flashed in accordance with a user specified frequency. Alternately, the confidence indicator will be disabled and not flashed.

As noted above, the method 100 can be carried out by the detector 10 substantially simultaneously with carrying out the normal gas and environmental sensing operations of that detector. Thus, even in the absence of the confidence indicating LED 34 being activated, the display 30 continues to provide visual information and the alarm indicting vibrator 32a, beeper 32b and LEDs 32c continue to be energized to indicate sensed alarm conditions.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

The invention claimed is:

1. A gas detector comprising:
a housing;
control circuits carried within the housing;
a plurality of sensors coupled to the control circuits and carried within the housing, wherein each of the plurality of sensors is configured to sense a different ambient condition according to a different sensing technology;
a compliance indicator, carried by the housing and coupled to the control circuits, the compliance indicator configured to emit a visual alarm having a first emitted color at a predetermined frequency; and
an alarm condition indicator, carried by the housing and coupled to the control circuits, the alarm condition indicator configured to emit an aural alarm or another visual alarm having a second emitted color in response to an alarm condition,
wherein the control circuits are configured, while at least one sensor of the plurality of sensors simultaneously senses according to a respective sensing technology, to:
determine whether a previous calibration attempt had been successful for each of the plurality of sensors,
establish a first pre-set time interval until the next calibration attempt is to be made for each of the plurality of sensors when the previous calibration attempt was successful for each of the plurality of sensors,
determine whether a previous bump test had been successful for each of the plurality of sensors,
establish a second pre-set time interval until the next bump test is to be made for each of the plurality of sensors when the previous bump test was successful for each of the plurality of sensors,
determine if the at least one sensor of the plurality of sensors senses an unsafe ambient condition,
in an instance in which the previous calibration attempt had been successful for each of the plurality of sensors, the first pre-set time interval has not expired for each of the plurality of sensors, the previous bump test had been successful for each of the plurality of sensors, and the second pre-set time interval has not expired for each of the plurality of sensors, activate the compliance indicator to indicate that each of the plurality of sensors of the gas detector is in compliance with pre-established calibration requirements and with pre-established bump test requirements, and
in an instance in which the at least one sensor of the plurality of sensors senses an unsafe ambient condition, the calibration test attempt fails for any one of the plurality of sensors, the bump test attempt fails for any one of the plurality of sensors, the first predetermined time interval has lapsed without a new calibration attempt for any one of the plurality of sensors, or the second predetermined time interval has lapsed without a new bump test attempt for any one of the plurality of sensors, activate the alarm condition indicator and either not activate the compliance indicator or deactivate the compliance indicator.

2. The detector as in claim 1, wherein the control circuits comprise a programmable processor and associated parameter storage, and wherein the programmable processor is configured to evaluate pre-stored calibration information to determine if a prior calibration attempt had been successful for each of the plurality of sensors.

3. The detector as in claim 2, further comprising:
a memory stored within the housing,
wherein the memory is configured to store control software, the control software being configured to carry out activation or deactivation of the compliance indicator and the alarm condition indicator in combination with the programmable processor.

4. The detector as in claim 2, where the processor, in executing the control software, evaluates gas concentration information received from the plurality of sensors in addition to previous calibration attempt information, first pre-set time interval timer information, previous bump test information, and second pre-set time interval timer information to determine whether said alarm condition exists.

5. The detector as in claim 4, which includes a multi-dimensional display device, and where the control circuits are further configured to activate the display device to provide visual gas concentration information substantially simultaneously with intermittently activating the compliance indicator.

6. The detector as in claim 5, which includes a real-time clock which is coupled to the control circuits, wherein the control circuits, in combination with pre-stored calibration information, established when the next calibration process is to be carried out.

7. The detector as in claim 1, further comprising:
at least a first compliance indicator and a second compliance indicator.

8. The detector as in claim 7, wherein the first compliance indicator and a second compliance indicator are different.

9. The detector as in claim 8, where the first compliance indicator and a second compliance indicator are configured to emit different types of compliance indicating indicia.

10. The detector as in claim 9, where at least some of the compliance indicating indicia are visual.

11. The detector as in claim 1, where the control circuits are configured to programmatically determine whether the previous calibration attempt had been successful for each of the plurality of sensors, programmatically establish the first pre-set time interval until the next calibration attempt is to be made for each of the plurality of sensors when the previous calibration attempt was successful for each of the plurality of sensors, programmatically determine whether the previous bump test had been successful for each of the plurality of sensors, programmatically establish the second pre-set time interval until the next bump test is to be made for each of the plurality of sensors when the previous bump test was successful for each of the plurality of sensors, and programmatically determine if the at least one sensor of the plurality of sensors senses an unsafe ambient condition.

12. The detector as in claim 1, where the control circuits are configured to:
- determine, after the first pre-set time interval has elapsed, whether a subsequent calibration attempt has been successful for each of the plurality of sensors,
- establish a third pre-set time interval until the next calibration attempt is to be made for each of the plurality of sensors when the subsequent calibration attempt was successful for each of the plurality of sensors,
- determine, after the second pre-set time interval has elapsed, whether a subsequent bump test had been successful for each of the plurality of sensors, and
- establish a fourth pre-set time interval until the next bump test is to be made for each of the plurality of sensors when the subsequent bump test was successful for each of the plurality of sensors.

* * * * *